United States Patent [19]
Gardineer et al.

[11] Patent Number: 5,967,991
[45] Date of Patent: Oct. 19, 1999

[54] DRIVE APPARATUS FOR AN INTERVENTIONAL MEDICAL DEVICE USED IN AN ULTRASONIC IMAGING SYSTEM

[75] Inventors: Bayard Gardineer, Skillman; John W. Bogan, Bedminster, both of N.J.

[73] Assignee: Echocath, Inc., Monmouth Junction, N.J.

[21] Appl. No.: 08/759,762

[22] Filed: Dec. 3, 1996

[51] Int. Cl.$^6$ .................................................. A61B 8/12
[52] U.S. Cl. ........................................... 600/461; 600/567
[58] Field of Search .................... 600/461, 471, 600/567; 606/1, 169; 604/22

[56] References Cited

U.S. PATENT DOCUMENTS

| | | | |
|---|---|---|---|
| 3,990,452 | 11/1976 | Murry et al. | 601/2 |
| 4,425,115 | 1/1984 | Wuchinich | 601/2 |
| 4,431,006 | 2/1984 | Trimmer et al. | 600/461 |
| 4,961,424 | 10/1990 | Kubota et al. | 601/2 |
| 5,095,910 | 3/1992 | Powers | 600/461 |
| 5,329,927 | 7/1994 | Gardineer et al. | 600/461 |
| 5,421,336 | 6/1995 | De Bernardis | 600/461 |
| 5,549,112 | 8/1996 | Cockburn et al. | 600/461 |

Primary Examiner—Francis J. Jaworski
Attorney, Agent, or Firm—Arthur L. Plevy

[57] ABSTRACT

A disposable interventional medical device assembly for use with a color ultrasonic imaging system or other ultrasonic systems sensitive to motion. The assembly includes an interventional medical device having an elongated member for insertion into an interior region of a body under investigation, and piezo driver assembly coupled to the member of the interventional medical device. The driver assembly produces a vibratory oscillation which causes the member to exhibit a flexural motion in response thereto, the flexural motion having a zero amplitude point and a maximum amplitude point, wherein the driver assembly is coupled to the member at a point located between the zero amplitude point and the maximum amplitude point of the member's flexural motion. In one embodiment of the present invention, the interventional medical device can be a biopsy needle wherein the elongated member is the shaft of the biopsy needle. Also described is an ultrasonic imaging system which includes the earlier described disposable interventional medical device assembly and a scanner for detecting the flexural motion of the member of the disposable interventional medical device when the member is inserted into an interior region of a body under investigation. The system generate an image of the interior region of the body under investigation in which the flexural motion is locatively represented.

27 Claims, 5 Drawing Sheets

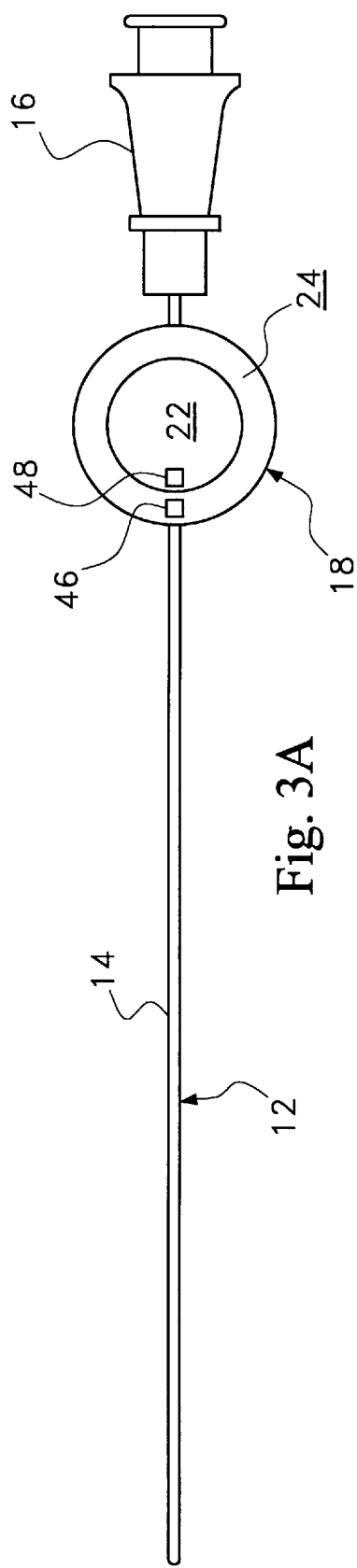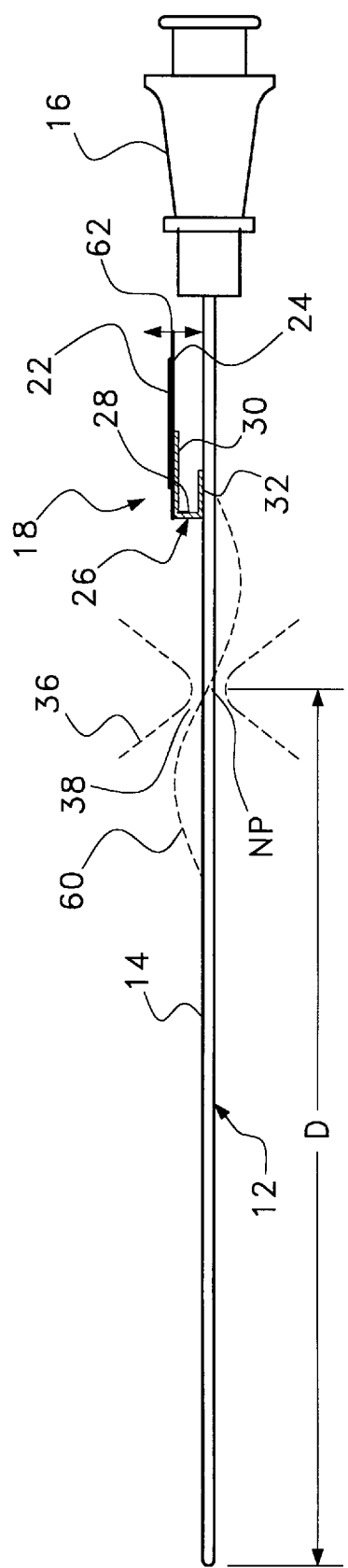

DRIVE APPARATUS FOR AN INTERVENTIONAL MEDICAL DEVICE USED IN AN ULTRASONIC IMAGING SYSTEM

FIELD OF THE INVENTION

The present invention relates to ultrasound imaging systems and more particularly, to an interventional medical device having a built-in vibrating driver assembly for use with an ultrasonic imaging system.

BACKGROUND OF THE INVENTION

Various ultrasonic imaging techniques are presently used by physicians for viewing internal regions of the human body. For example, ultrasonic imaging techniques are used for detecting potentially malignant tumors. When a tumor is detected, it is desirable to take a tissue sample of the tumor and perform a biopsy of the sample to determine whether it is malignant. In many cases, the tissue sample is extracted in a minor surgical procedure which involves the insertion of a biopsy needle into the body of the patient and directing the needle toward the tumor. In such a procedure, the physician inserts a biopsy needle into the body of a patient and guides it toward the tissue to be biopsied by watching an image of the internal region of interest in the patient's body produced by the ultrasonic imaging system. During such a procedure, the physician must be able to clearly visualize the needle in order to accurately guide it through the patient's body toward the area of tissue to be removed by the biopsy needle.

In order to monitor the biopsy needle within the body using ultrasonic imaging techniques, the needle must be coupled to an ultrasonic transducer which causes the needle to transmit and/or receive ultrasonic waves in cooperation with an imaging scanhead. For example, U.S. Pat. No. 3,556,079 issued to Omizo discloses a method whereby Doppler interrogating waves are directed forward from the tip of a biopsy needle. As the needle penetrates the body, backscatter waves from moving fluids within a vessel or organ are received and a conventional Doppler beat frequency is detected. The reception of the Doppler tone provides an indication that the needle is aimed at the vessel or organ containing the fluid. The Omizo method is a highly directional method and consequently, if the needle becomes misdirected, no backscatter waves will be returned thereby causing the Doppler tone to cease.

In U.S. Pat. No. 4,249,539 issued to Vilkomerson et al., a system is disclosed which includes an omnidirectional transducer located at the needle tip. The transducer is used as a transponder to send signals back through the body to a transmitter when a signal is detected. The omnidirectional transducer exchanges ultrasonic waves with the imaging transducer irrespective of the orientation of the omnidirectional transducer, thus enabling the system to continually provide a visual marker in the ultrasonic image which indicates the needle tip location. An ultrasonic imaging transducer provides a two-dimensional image as it scans a relatively planar portion of the patient's body. Consequently, the needle tip can only be visualized when it is located within the scan plane of the imaging transducer. Hence, the '539 system cannot visualize the needle tip when the physician first enters the body if the plane of penetration is outside of the scan plane of the imaging transducer. When this occurs, the physician is required to focus his attention on the insertion and guidance of the biopsy needle and at the same time manipulate the imaging transducer and watch the imaging monitor to simultaneously orient the transducer and the needle so that the tissue structure to be biopsied and the needle tip are in the image or scan plane.

In U.S. Pat. No. 5,095,910 issued to Powers, a biopsy needle with a reciprocating tip that produces a highly directional motion is described. The highly directional motion produces a Doppler shift which is detected and displayed by a color ultrasonic imaging system. As a result, the needle tip can be monitored as it is guided toward the tissue to be biopsied. The biopsy needle in the '910 patent comprises an inner solid element or stylet which reciprocates longitudinally within a hollow tube or cannula. The only motion that appears in the ultrasonic colorflow image as a visual Doppler response is the motion of the tip of the stylet at the open end of the cannula. This motion is shown as color. The system will not show the tip of the stylet if the tissue is liquid in nature, such as in the necrotic center of tumors, or when the stylet tip is at right angles to the ultrasound beam. The reciprocating motion is provided by a driver in the hub of the needle. As such, this arrangement is limited to specially prepared needles or other such devices for use in this system.

In U.S. Pat. No. 5,329,927, issued to Gardineer et al., a color ultrasonic imaging system for visualizing the tip of an interventional medical device, such as a biopsy needle, in the body of a patient is described. The patent describes an apparatus and method for causing a periodic or oscillating mechanical motion in the form of flexural waves in the X, Y, and Z axes in the needle which results in a significant Doppler shift effect that enables the needle to be detected by the color ultrasonic imaging system. The needle is made to oscillate by a mechanical motion mechanism or VIBER coupled thereto. The needle is coupled and secured to the mechanical motion mechanism using a flexible clip-like element formed from any suitable metal or plastic material. The flexible clip-like element is designed to accommodate and secure needles of different gages to the mechanical motion mechanism. Problems, however, having to do with assured fixation of the needle to the mechanical motion mechanism still arise due to the fixed diameter of the flexible clip-like element which works well only with a narrow range of needle gages. Moreover, the mechanical motion mechanism is generally expensive to manufacture.

Accordingly there is a need to provide interventional medical devices with their own built-in, high quality, low cost vibrating driver assembly which enables the interventional medical device to be utilized in a color ultrasonic imaging system, or a black and white system as taught in U.S. Pat. No. 5,425,370 by Vilkomerson.

SUMMARY OF THE INVENTION

A disposable interventional medical device assembly for use with a color or black and white ultrasonic imaging system, comprising an interventional medical device having an elongated member for insertion into an interior region of a body under investigation, and vibrator means coupled to the member of the interventional medical device. The vibrator means produces a vibratory oscillation which causes the member to exhibit a flexural motion in response thereto, the flexural motion having a zero amplitude point and a maximum amplitude point, wherein the vibrator means is coupled to the member at a point located between the zero amplitude point and the maximum amplitude point of the member's flexural motion.

In one embodiment of the present invention, the interventional medical device comprises a biopsy needle wherein the elongated member comprises a shaft of the biopsy needle.

Also described is an ultrasonic imaging system comprising the earlier described disposable interventional medical device assembly. The system also comprises scanning means for detecting the flexural motion of the member of the disposable interventional medical device when the member is inserted into an interior region of a body under investigation and ultrasonic imaging means for generating an image of the interior region of the body under investigation in which the flexural motion is locatively represented.

BRIEF DESCRIPTION OF THE DRAWINGS

For a detailed understanding of the present invention, reference should be made to the following detailed description taken in conjunction with the accompanying drawings wherein:

FIG. 3A is a top plan view of the biopsy needle assembly made according to the present invention without the housing and the housing cover;

FIG. 3B is side elevational view of the biopsy needle assembly of FIG. 3A;

DETAILED DESCRIPTION OF THE INVENTION

Current medical practice dictates that biopsy needles, which are commonly used in surgical procedures that require visualization via conventional color ultrasound systems, be manufactured in various diameters, lengths, and cutting tip designs. It is extremely desirable from an economic standpoint, to be able to construct and manufacture these biopsy needles with their own vibrating driver. For example, such biopsy needles typically range in gages from 16 (1.6 mm diameter) to 25 (0.4 mm diameter), come in lengths from 0.5 inches to 10 inches, and have straight or various angled slant-cut cutting tips. Accordingly, the vibrating driver assembly of the present invention will be described in application to biopsy needles. It should be understood, however, that the vibrating driver apparatus of the present invention can be applied to other beam-like interventional medical devices, such as catheters and the like, which are commonly monitored in surgical procedures using color ultrasonic imaging systems.

Figure 1A:
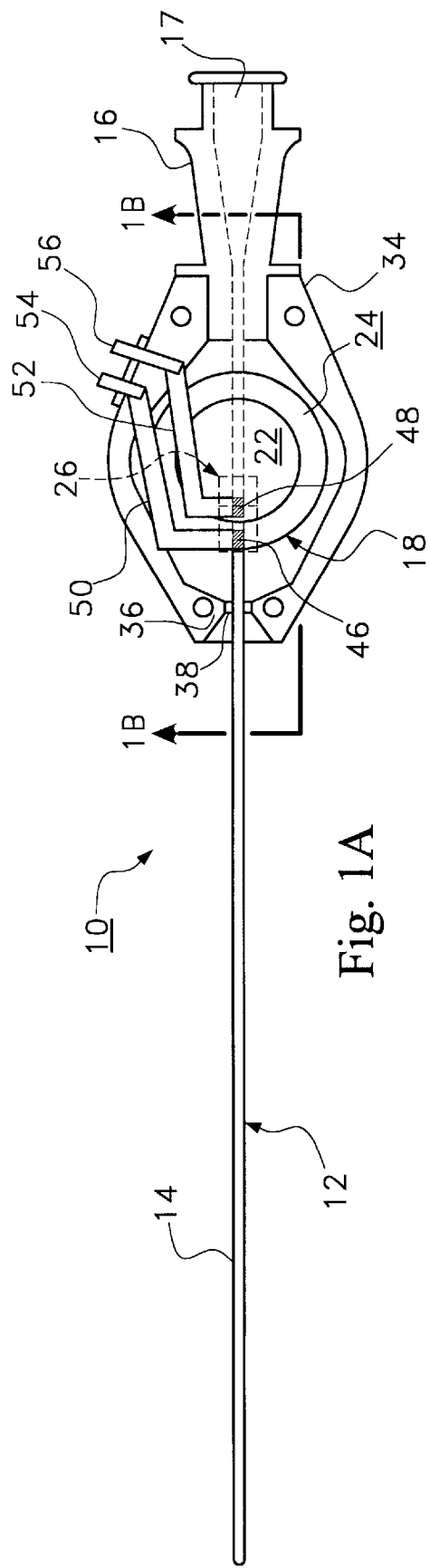
FIG. 1A is a top plan view of a biopsy needle assembly made in according to the present invention with the housing cover removed.
Figure 1B:
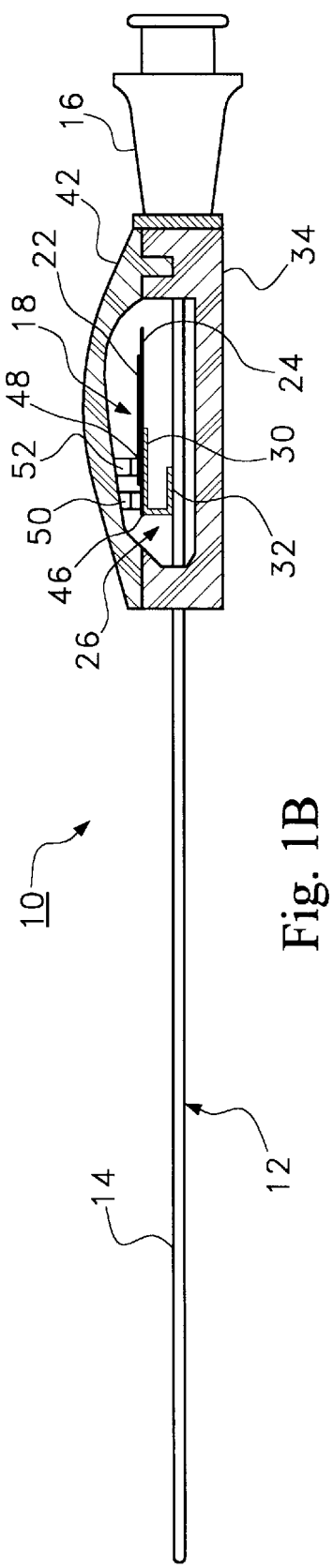
FIG. 1B is a cross-section side view through line 1B—1B of the housing of the biopsy needle assembly of FIG. 1A.
Figure 5:
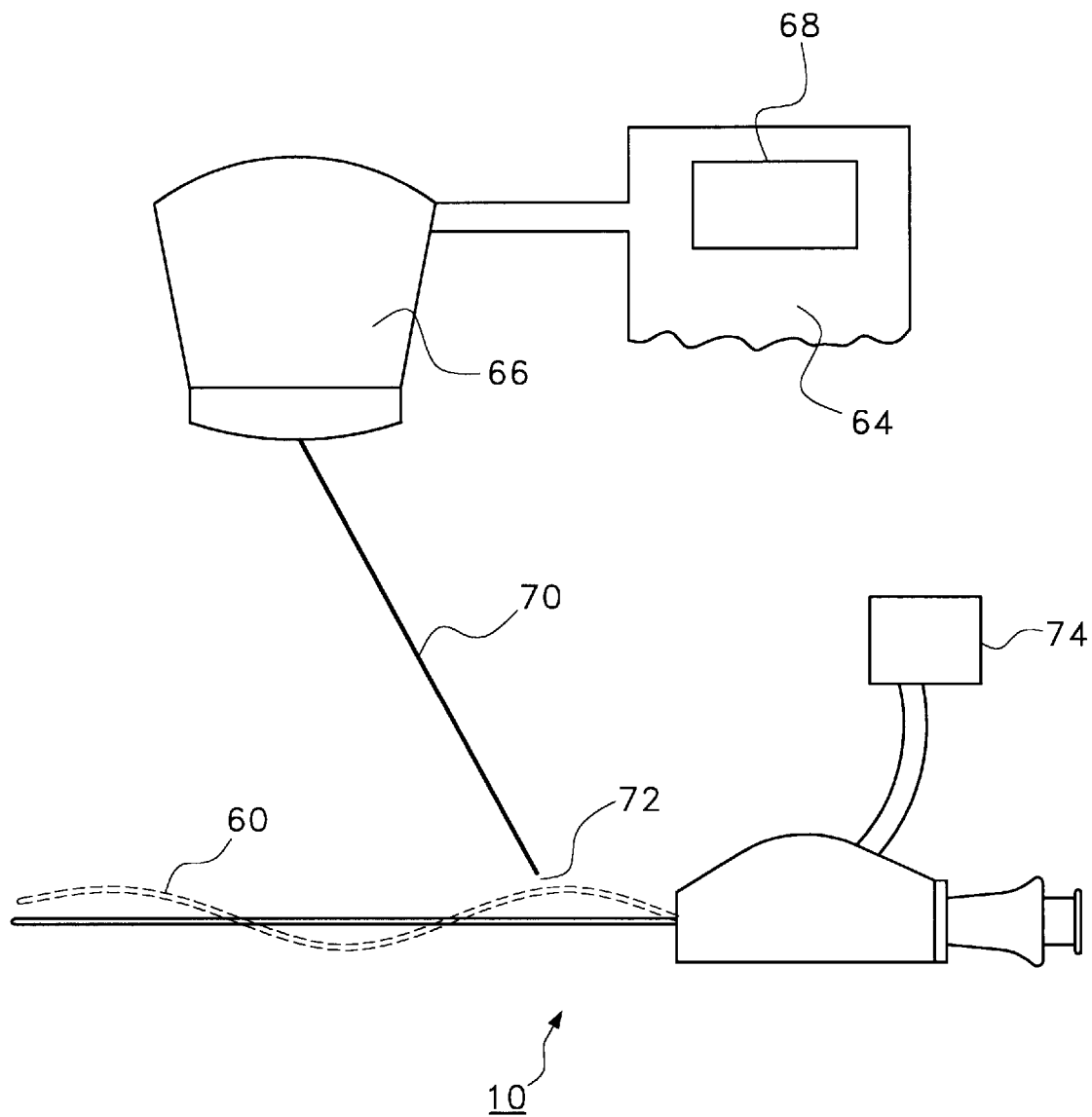
FIG. 5 is a pictorial representation of an ultrasound imaging system for transmitting the flexural motion of the biopsy needle assembly made according to the present invention.

Referring collectively to FIGS. 1A and 1B, a biopsy needle assembly 10 made in accordance with the present invention is depicted. The biopsy needle assembly 10 generally comprises a biopsy needle 12 powered by a vibrating piezo driver assembly 18. The biopsy needle 12 has a shaft 14 which is fixed at one end in a hub 16. The hub 16 of the biopsy needle 12 contains a conical opening or luer connection 17 which allows the needle 12 to be connected to other medical apparatus such as tube and plunger devices used to propel liquids or extract liquid or tissues from the site of the needle insertion. The portion of the biopsy needle assembly 10 that vibrates and forms a standing wave is the thin, hollow tube or cannula, which forms the shaft 14. (In other embodiments, only the stylet may be energized.) The piezo driver assembly 18 is a piezoelectric acoustic transducer (unimorph) comprising a single disc-shaped transducer 22 of piezoelectric ceramic bonded to a circular-shaped metal plate 24 composed of brass, stainless steel or any other suitable metal. The piezoelectric ceramic typically comprises some type of modified lead zirconate (PZT) composition or to a lesser extent, some type of modified barium titanate composition. Piezoelectric acoustic transducers made from such materials are well known in art and offer a high quality, low cost drive for the needle. Other embodiments of the present invention, the driver assembly 18 can comprise magnetic transducers and the like. In any case, the piezo driver assembly 18 is preferably coupled to the shaft 14 of the needle 10 via high rate a spring-like coupler bracket 26 (shown with broken lines) as will be explained later on in greater detail. The piezo driver assembly 18 is enclosed in a piezo driver housing 34 that is coupled to the hub 1 of the needle 12. The housing 34 includes a needle restrictor ring portion 36 that defines an aperture 38 through which the shaft 14 of the needle 12 extends out through the housing 34. A cover 42 for the housing 34 is provided and may be aligned to the housing 34 by pins, edges, depressions or other methods commonly employed. The housing 34 may also be fabricated in such a manner as to include the hub portion 16 where the luer connection 17 is constructed. A pair of leads 50, 52 attach the piezo driver assembly 18 to a pair of connectors 54, 56 mounted on the housing 22. The connectors 54, 56 enable the piezo driver assembly 18 contained within the housing 34 to be electrically coupled to an oscillator circuit 74 which activates the piezo driver assembly (FIG. 5). Such an oscillator circuit is described in U.S. Pat. No. 5,329,927, the entire disclosure of which is incorporated herein by reference. The leads 50, 52 are coupled to the piezo driver assembly 18 via an electrode 46 located on the metal plate 24 and an electrode 48 located on the surface of the ceramic transducer 22. It is preferred that the leads 50, 52 be of the solderless, detachable type so that they can be easily removed from both the piezo driver assembly 18 and the connectors 54, 56 mounted on the housing 34 without unsoldering. The electrodes 46 and 48 of the piezo driver assembly are best seen in FIG. 3A which depicts a top view of needle assembly 10 without the housing 34 and housing cover 42. As an alternative to this construction, the wire leads from the driver assembly may also be introduced into the housing directly and the leads soldered to points 46 and 48

Figure 2A:
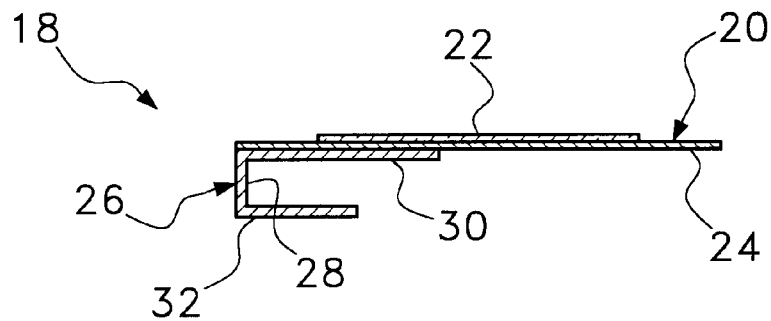
FIG. 2A is a cross-sectional side view of the piezo driver assembly of the biopsy needle assembly coupled to a spring-like coupler bracket.
Figure 2B:
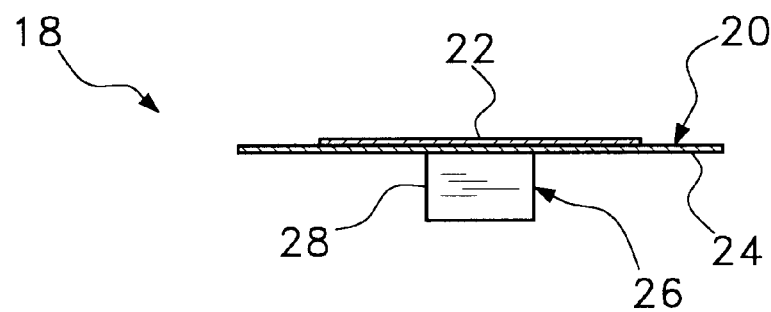
FIG. 2B is a front elevational view of the piezo driver assembly of FIG. 2A.
Figure 2C:
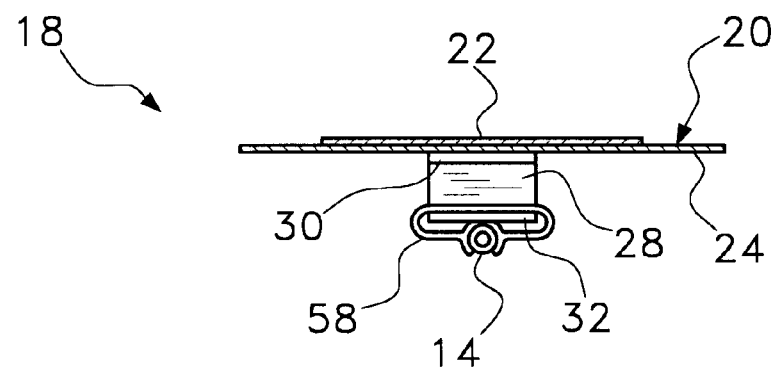
FIG. 2C is a rear elevational view of the piezo driver assembly of FIG. 2B coupled to the shaft of the biopsy needle.

FIGS. 1B, 2A and 2B, depicts the spring-like coupler bracket 26 which couples the piezo driver assembly 18 to the needle 12 in the preferred embodiment of the invention. As shown, the coupler bracket 26 has an asymmetrically-shaped configuration consisting of an elongated support member 28 with a first arm 30 hingedly attached to one end of the member 28 and second arm 32 hingedly attached to the other end of the member 28. The first arm 30 has a substantially greater length than the second arm 32. The coupler bracket 26 is preferably made from stainless steel although any other suitable material can be used. The piezo driver assembly 18 is adhesively bonded to the first arm 30 of the coupler bracket 26. The second arm 32 of the coupler bracket 26 is adhesively bonded or welded to the shaft 14 of the needle 12. In other embodiments such as the one shown in FIG. 2C, a separate clip-like fastening element 58 is used to fasten the second arm 32 to the shaft 14 of the needle 12. Alternatively, the second arm 32 of the coupler bracket 26 can be configured to clip over the shaft 14 of the needle 12. In such an embodiment, glue can be optionally used to prevent detachment of the coupler bracket 26 from the needle 12. In all of the above embodiments, the coupler bracket 26 operates as a lever to impart a torque on the shaft 14 of the needle 12 as will be further explained below. Further, the coupler bracket 26 also prevents the piezo driver assembly 18 from breaking away from the needle 12 in the event that the shaft 14 of the needle 12 is bent during use. It should be understood, however, that the piezo driver assembly 18 can be bonded directly to the shaft 12 of the needle 10 without the coupler bracket 26 if desired. Referring now to FIG. 3B, there is depicted a side view of the needle assembly 10 without the housing 34 and housing cover 42. The needle restrictor ring portion 36 (shown in phantom with broken lines) limits how much the shaft 14 of the needle 12 can bend as the shaft 14 of the needle 12 is inserted and guided through a patient's body by a physician. For example, if the shaft 14 of the needle 12 is approximately 0.027 of an inch, the diameter of the aperture 38 provided by the needle restrictor ring portion 36 would be approximately 0.080 of an inch. The housing 34 is configured so that the restrictor ring portion 36 surrounds the shaft 14 of the needle 12 at a point which provides a satisfactory needle working length. The working length of the needle 12 is the distance D from the restrictor ring portion 36 to the tip of the shaft 14. Typical working lengths range between 7.5 cm to 3 inches. The location of the restrictor ring portion 36 must also approximately coincide with a vibrational null point NP of an exaggerated wave 60 which represents the flexure of the needle 12 at its natural resonance frequency. Placing the restrictor ring portion 36 close to the null point NP operates to reduce the amount of damping to the needle 12 when the needle 12 is bent and makes contact with the needle restrictor ring portion 36. Since the natural resonance frequency of the needle 12 is dependent upon the length of the needle, which is controlled by the desired working length, the location of the restriction ring portion 36 from the hub 16 of the needle 12 can be determined.

The piezo driver assembly 18 used in the present invention has a natural resonance frequency on the order of approximately 5000 Hz. The biopsy needles 12 used in the present invention have a preferred natural resonance frequency of 2700 Hz and a preferred resonance frequency range of between 2100 and 2700 Hz depending on the length of the needle's shaft 14. Accordingly, the piezo driver assembly 18 is capable of driving the needle 12 at any desired frequency without interference from the undesirable natural frequencies of the piezo driver assembly 18.

In FIG. 3B, the piezo driver assembly 18 is shown attached to the shaft 14 of the needle 12 via the spring coupler bracket 26 at a location which is selected to be at a point P which is approximately midway between the vibrational null point NP and a vibrational maximum point MP of the needle 12 depicted by the wave 60. The exact location of the piezo driver assembly 18 on the needle 12 is not as critical in terms of the needle assembly 10 producing a desired output (amplitude of needle vibration) compared with the arrangement described in U.S. Pat. No. 5,329,927 where the driver assembly must be mounted almost exactly at the vibrational maximum point of the needle.

Still referring to FIG. 3B, when the piezo driver assembly 18 is driven at resonance, the portion of the assembly farthest from the point where the first arm 30 and the elongated support member 28 are hinged, pivotally vibrates primarily in an up and down motion as shown by arrow 62. This up and down motion causes the first arm 30 to operate as a lever to impart a torque on the shaft 14 of the needle 12 as well as a force which causes the shaft 14 of the needle 12 to exhibit flexural vibrations in primarily one plane (referred to as X for illustrative purposes). In comparison, the driver arrangement described in U.S. Pat. No. 5,329,927 applies only a force to the needle. Accordingly, the driver assembly in U.S. Pat. No. 5,329,927 must be mounted almost exactly at the vibrational maximum point of the needle as discussed above.

The phrase "flexural vibrations" which is used to describe the motion of the needle 12, denotes the curving or "flexure" of the needle's shaft 14 which is generated by the wave-like characteristics of the mechanical energy transmission generated by the piezo driver assembly 18 as depicted by the wave 60. Flexure occurs in an elastic material when a deflection is suitable to set-up stresses in the material. The vibratory-induced flexural waves operate and exhibit characteristics similar to standing waves or as propagating waves. Since the piezo driver assembly 18 also vibrates in the Y and Z planes, the shaft 14 of the needle 12 also exhibits flexural vibrations in the Y and Z planes. The flexural waves provided by the piezo driver assembly 18 are transmitted about or along the X,Y and/or Z axes at synchronized, but non-harmonically related frequencies that correspond to resonant frequencies of the needle 12. A more detailed discussion of biopsy needles and other interventional devices which are made to exhibit flexural waves is provided in the earlier mentioned U.S. Pat. No. 5,329,927.

Figure 4:
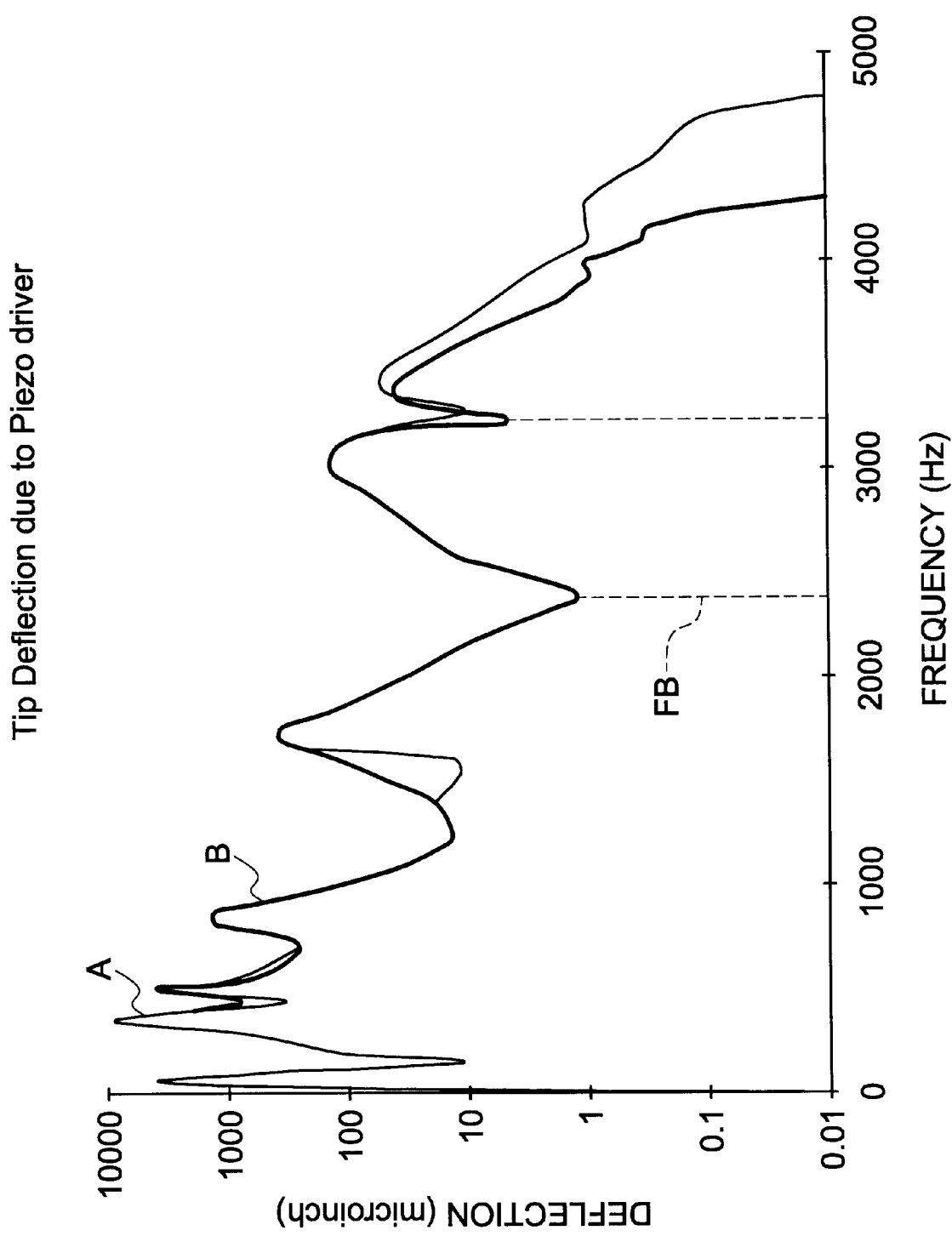
FIG. 4 is a graph which depicts tip deflection of the biopsy needle assembly made according to the present invention, due to the piezo driver.

FIG. 4 depicts the tip deflection of the needle 12 when driven by a piezo driver assembly 18 attached to the shaft 14 thereof with and without the coupler bracket 26 at frequencies up to approximately 5000 Hz. The curve A corresponds to the instrumented output of the piezo driver assembly 18 attached via a coupler bracket 26. The curve B corresponds to the the frequencies calculated from a 3-d model constructed in software available from SDRC called I-DEAS, and analyzed by SDRC's finite element analysis software. Note that both the device and the model exhibit approximately 4 different frequency bands of resonance, the fourth frequency band FB occurring between approximately 2300 Hz and 3300 Hz and being the preferred resonance frequency range for operating the needle assembly 10.

Accordingly, as depicted in FIG. 5, a conventional color ultrasonic imaging system comprising an ultrasonic imaging device 64, a scanner 66 electrically coupled to the imaging device 64 and the biopsy needle assembly 10 made according to the present invention. The ultrasonic imaging device via the scanner 66 can detect Doppler movements resulting from the flexural waves 60 exhibited by the needle assembly 10 of the present invention in any of the X, Y and Z planes thereby providing a precise indication on a display 68 of the system 64 as to the location of the needle assembly 10 within a patient. The scanner 66 impresses an imaging pulse 70 on a point 72 of the biopsy needle assembly 10. As an example of operation, the point 72 may be closest to the scan head 66 when the first imaging pulse 70 occurs and furthest when a second imaging pulse 70 occurs. Known imaging systems 64 are able to detect and display the velocity of a moving element in the 0.2–100 centimeters per second or more (cm/sec) range. In order to accomplish this, the first and second imaging pulses 70 are produced typically every 80 to 330 microseconds (usec) depending on the scale of the velocity to be detected. If a 5 cm/sec velocity is detected with a sampling interval of the imaging pulses set at 118 microseconds, the detected displacement of the point 72 is 5 centimeters/second times 118 microseconds, or approximately 6 microns. Therefore, as indicated above, small vibratory motions, on the order of microns, can be detected by known colorflow imaging systems or by the method disclosed in U.S. Pat. No. 5,425,370 issued to Vilkomerson and assigned to EchoCath, Inc., the assignee herein.

As should be apparent, that the driving method of the present invention provides a simple, easy to manufacture, low cost approach for driving an interventional medical device, such as a biopsy needle, into sustained oscillation. Accordingly, the driving method of the present invention provides inexpensive, throw away beam-like interventional medical devices such is biopsy needles with excellent visibility under color ultrasound scans.

It should be understood that the embodiments described herein are merely exemplary and that a person skilled in the art may make many variations and modifications to these embodiments utilizing functionally equivalent elements to those described herein. Any and all such variations or modifications as well as others which may become apparent to those skilled in the art, are intended to be included within the scope of the invention as defined by the appended claims.

What is claimed is:

1. A disposable needle assembly for use with an ultrasonic imaging system, comprising:
   a needle including an elongated member for insertion into an interior region of a body under investigation;
   vibrator means for producing a vibratory oscillation which causes said member to exhibit a flexural motion in response thereto, said flexural motion having a zero amplitude point and a maximum amplitude point; and,
   a bracket comprising a support element including first and second ends, a first arm coupled to said vibrator means and hingedly attached to said first end of said support element and a second arm coupled to said elongated member and hingedly attached to said second end of said support element;
   wherein said first arm is substantially longer than said second arm and said first arm is coupled to said member at a point located between said zero amplitude point and said maximum amplitude point of said flexural motion.

2. The disposable needle assembly according to claim 1, wherein vibratory oscillations produced by said vibrator means are applied to said member by said bracket.

3. The disposable needle assembly according to claim 2, wherein said first arm is integrally attached to said vibrator means and said second arm is integrally attached to said member of said needle.

4. The disposable needle assembly according to claim 2, wherein said first arm is integrally attached to said vibrator means and said second arm is removably fastened to said member of said needle.

5. The disposable needle assembly according to claim 1, wherein said vibrator means comprises a transducer.

6. The disposable needle assembly according to claim 5, wherein said transducer comprises a disc-shaped piezoelectric ceramic bonded to a metal plate.

7. A disposable biopsy needle assembly for use with an ultrasonic imaging system, comprising:
   a biopsy needle having a shaft for insertion into an interior region of a body under investigation;
   vibrator means coupled to said shaft of said biopsy needle, for producing a vibratory oscillation which causes said shaft to exhibit a flexural motion in response thereto, said flexural motion having a zero amplitude point and a maximum amplitude point; and,
   a bracket comprising a support element including first and second ends, a first arm coupled to said vibrator means and hingedly attached to said first end of said support element and a second arm coupled to said elongated member and hingedly attached to said second end of said support element;
   wherein said first arm is longer than said second arm and said first arm is coupled to said shaft at a point located between said zero amplitude point and said maximum amplitude point of said flexural motion.

8. The disposable biopsy needle assembly according to claim 7, further comprising a housing which encloses said vibrator means.

9. The disposable biopsy needle assembly according to claim 8, wherein said housing encloses a portion of said biopsy needle, said housing including restrictor means for limiting the bending of said shaft of said biopsy needle when said shaft is manipulated in an interior region of a body under investigation.

10. The disposable biopsy needle assembly according to claim 9, wherein said restrictor means surrounds said shaft at said zero amplitude point of said shaft's flexural motion to reduce the amount of damping to said biopsy needle when said shaft is bent and makes contact with said restrictor means.

11. The disposable biopsy needle assembly according to claim 7, further comprising means for electrically coupling said vibrator means to an externally located oscillator circuit which activates said vibrator means.

12. The disposable biopsy needle assembly according to claim 7, wherein said biopsy needle includes a hub, said shaft having one end fixed in said hub.

13. The disposable biopsy needle assembly according to claim 7, wherein vibratory oscillations produced by said vibrator means are applied to said shaft by said bracket as a torque and a force which cause said shaft to exhibit said flexural motion.

14. The disposable biopsy needle assembly according to claim 13, wherein said first arm is integrally attached to said vibrator means and said second arm is integrally attached to said shaft of said biopsy needle.

15. The disposable biopsy needle assembly according to claim 13, wherein said first arm is integrally attached to said vibrator means and said second arm is removably fastened to said shaft of said biopsy needle.

16. The disposable biopsy needle assembly according to claim 7, wherein said vibrator means comprises a transducer.

17. The disposable biopsy needle assembly according to claim 16, wherein said transducer comprises a disc-shaped piezoelectric ceramic bonded to a metal plate.

18. An ultrasonic imaging system comprising:
   a disposable needle assembly including a disposable needle with an elongated member for insertion into an interior region of a body under investigation, vibrator means for producing a vibratory oscillation which causes said member to exhibit a flexural motion in response thereto, said flexural motion having a zero amplitude point and a maximum amplitude point, and, a bracket comprising a support element including first and second ends, a first arm coupled to said vibrator means and hingedly attached to said first end of said support element and a second arm coupled to said elongated member and hingedly attached to said second end of said support element; wherein said first arm is coupled to said member at a point located between said zero amplitude point and said maximum amplitude point of said flexural motion;

scanning means for detecting said flexural motion of said member of said disposable needle when said member is inserted into an interior region of a body under investigation; and ultrasonic imaging means for generating an image of the interior region of the body under investigation in which said flexural motion is locatively represented.

19. The ultrasonic imaging system according to claim 18, wherein vibratory oscillations produced by said vibrator means are applied to said member by said coupler bracket as a torque and a force which cause said member to exhibit said flexural motion.

20. The ultrasonic imaging system according to claim 18, wherein said vibrator means comprises a transducer.

21. The ultrasonic imaging system according to claim 20, wherein said transducer comprises a disc-shaped piezoelectric ceramic bonded to a metal plate.

22. The ultrasonic imaging system according to claim 18, wherein said needle comprises a biopsy needle and said elongated member comprises a shaft of said biopsy needle.

23. The ultrasonic imaging system according to claim 22, wherein said needle assembly further comprises a housing which encloses said vibrator means.

24. The ultrasonic imaging system according to claim 23, wherein said housing encloses a portion of said biopsy needle, said housing including restrictor means for limiting the bending of said shaft of said biopsy needle when said shaft is manipulated in an interior region of a body under investigation.

25. The ultrasonic imaging system according to claim 24, wherein said restrictor means surrounds said shaft at said zero amplitude point of said shaft's flexural motion to reduce the amount of damping to said biopsy needle when said shaft is bent and makes contact with said restrictor means.

26. The ultrasonic imaging system according to claim 18, further comprising an oscillator circuit coupled to said vibrator means of said needle assembly for activating said vibrator means, and said needle assembly further comprising means for electrically coupling said vibrator means to an externally located oscillator circuit which activates said vibrator means.

27. A disposable needle assembly for use with an ultrasonic imaging system, said assembly comprising:

a needle including an elongated member for insertion into an interior region of a body under investigation; and vibrator means comprising a transducer comprising a disc-shaped piezoelectric ceramic bonded to a metal plate coupled to said elongated member of said needle, said vibrator means for producing a vibratory oscillation which causes said member to exhibit a flexural motion in response thereto, said flexural motion having a zero amplitude point and a maximum amplitude point;

wherein said vibrator means is coupled to said member at a point located between said zero amplitude point and said maximum amplitude point of said flexural motion.

* * * * *